US009941096B2

(12) United States Patent
Schmidt et al.

(10) Patent No.: US 9,941,096 B2
(45) Date of Patent: Apr. 10, 2018

(54) GLANCING ANGLE MILL

(75) Inventors: Michael Schmidt, Gresham, OR (US); Cliff Bugge, Portland, OR (US)

(73) Assignee: FEI Company, Hillsboro, OR (US)

( * ) Notice: Subject to any disclaimer, the term of this patent is extended or adjusted under 35 U.S.C. 154(b) by 1137 days.

(21) Appl. No.: 13/609,811

(22) Filed: Sep. 11, 2012

(65) Prior Publication Data
US 2013/0186747 A1 Jul. 25, 2013

Related U.S. Application Data

(60) Provisional application No. 61/533,769, filed on Sep. 12, 2011.

(51) Int. Cl.
| | | |
|---|---|---|
| G01N 1/28 | (2006.01) |
| H01J 37/30 | (2006.01) |
| H01J 37/305 | (2006.01) |

(52) U.S. Cl.
CPC .......... *H01J 37/3053* (2013.01); *G01N 1/286* (2013.01); *H01J 37/3005* (2013.01); *G01N 2001/2873* (2013.01); *H01J 2237/31745* (2013.01)

(58) Field of Classification Search
CPC ............ G01N 1/286; G01N 2001/2873; H01J 37/3053; H01J 37/3005; H01J 2237/31745
USPC .................................................... 204/192.34
See application file for complete search history.

(56) References Cited

U.S. PATENT DOCUMENTS

| | | | |
|---|---|---|---|
| 5,435,850 A | 7/1995 | Rasmussen | |
| 5,783,830 A * | 7/1998 | Hirose | H01J 37/3056 |
| | | | 250/442.11 |
| 5,851,413 A | 12/1998 | Casella et al. | |
| 7,161,159 B2 | 1/2007 | Hill et al. | |

(Continued)

FOREIGN PATENT DOCUMENTS

| | | |
|---|---|---|
| CN | 101153833 A | 4/2008 |
| CN | 201374309 | 12/2009 |

(Continued)

OTHER PUBLICATIONS

Liu, Xiangxin, et al., "Characterizing Thin Film PV Devices with Low-Incidence Surface Milling by Focused Ion Beam", Photovoltaic Specialists Conference (PVSC), 2011, 37th IEEE, pp. 1695-1699. Seattle, WA.

(Continued)

*Primary Examiner* — Rodney McDonald
(74) *Attorney, Agent, or Firm* — Scheinberg & Associates, P.C.; John B. Kelly; Michael O. Scheinberg

(57) ABSTRACT

A method and system for forming a planar cross-section view for an electron microscope. The method comprises directing an ion beam from an ion source toward a first surface of a sample to mill at least a portion of the sample; milling the first surface, using the ion beam, to expose a second surface in which the end of the second surface distal to the ion source is milled to a greater depth relative to a reference depth than the end of the first surface proximal to the ion source; directing an electron beam from an electron source to the second surface; and forming an image of the second surface by detecting the interaction of the electron beam with the second surface. Embodiments also include planarzing the first surface of the sample prior to forming a cross-section.

8 Claims, 8 Drawing Sheets

(56) References Cited

U.S. PATENT DOCUMENTS

| | | | |
|---|---|---|---|
| 7,442,924 B2 | 10/2008 | Giannuzzi et al. | |
| 7,601,976 B2 | 10/2009 | Hill et al. | |
| 7,858,936 B2 | 12/2010 | Bray et al. | |
| 8,013,311 B2 | 9/2011 | Hill et al. | |
| 2004/0232330 A1 | 11/2004 | Uenishi et al. | |
| 2006/0113496 A1 | 6/2006 | Yoshioka | |
| 2007/0158562 A1* | 7/2007 | Nasser-Ghodsi | H01J 37/28 250/310 |
| 2008/0073582 A1 | 3/2008 | Shichi et al. | |
| 2009/0020698 A1 | 1/2009 | Muto et al. | |
| 2011/0309263 A1 | 12/2011 | Hill et al. | |

FOREIGN PATENT DOCUMENTS

| | | |
|---|---|---|
| JP | 06-190569 | 7/1994 |
| JP | 6190569 | 7/1994 |
| JP | H10256332 | 9/1998 |
| JP | H11213935 | 8/1999 |
| JP | 2001217290 A | 8/2001 |
| JP | 2003-133203 | 5/2003 |
| JP | 2004219261 A | 8/2004 |
| JP | 2005122909 A | 5/2005 |
| JP | 2007250371 A | 9/2007 |
| JP | 2009026621 | 2/2009 |
| JP | 200959516 | 3/2009 |
| KR | 100226506 | 10/1999 |

OTHER PUBLICATIONS

Beckschaefer, Berthold, "Tomographic Orientation Microscopy (3D EBSD) Using a Joint FIB SEM Technique", Max-Planck-Institut fuer Eisenforschung GmbH, http://www.mpie.de/index.php?id=1056, last accessed Feb. 26, 2015.

Zaefferer, S., et al., "Three-Dimensional Orientation Microscopy in a Focused Ion Beam-Scanning Electron Microscope: A New Dimension of Microstructure Characterization," Metallurgical and Materials Transactions, Jan. 4, 2008, pp. 374-389, vol. 39A.

* cited by examiner

GLANCING ANGLE MILL

This Application claims priority from U.S. Provisional Application 61/533,769, filed Sep. 12, 2011, which is hereby incorporated by reference.

TECHNICAL FIELD OF THE INVENTION

The present invention relates to charged particle beam milling and, in particular, to a method of forming a planar cross section view for a scanning electron microscope.

BACKGROUND OF THE INVENTION

Charged particle beam systems are used in a variety of applications, including the manufacturing, repair, and inspection of micro-fabricated devices, such as integrated circuits, magnetic recording heads, and photolithography masks. Dual beam systems, such as the DualBeam instruments commercially available from FEI Company, the assignee of the present invention, typically include a scanning electron microscope (SEM) that can provide a high-resolution image with minimal damage to the target, and an ion beam system, such as a focused or shaped beam system (FIB), that can be used to alter substrates and to form images. Such deal beams systems are described, for example, in U.S. Pat. No. 7,161,159 to Hill, et al., which is incorporated by reference in its entirety in the present application. In some dual beam systems, the FIB is oriented an angle, such as 52 degrees, from the vertical and an electron beam column is oriented vertically. In other systems, the electron beam column is tilted and the FIB is oriented vertically or also tilted. The stage on which the sample is mounted can typically be tilted, in some systems up to about 60 degrees.

A common application for a dual beam system is analyzing defects and other failures during micro-fabrication to troubleshoot, adjust, and improve micro-fabrication processes. Defect analysis is useful in all aspects of semiconductor production including design verification diagnostics, production diagnostics, as well as other aspects of microcircuit research and development. As device geometries continue to shrink and new materials are introduced, the structural complexity of today's semiconductors grows exponentially. Many of the structures created with these new materials are re-entrant, penetrating back through previous layers. Thus, the defects and structural causes of device failure are often hidden well below the surface.

Accordingly, defect analysis often requires cross-sectioning and viewing defects on a three-dimensional basis. With the growing use of copper conductor devices on semiconductor wafers, better systems capable of performing three dimensional defect analyses are more important than ever. This is because there are more defects that are buried and/or smaller, and in addition, chemical analysis is needed in many cases. Moreover, structural diagnostics solutions for defect characterization and failure analysis need to deliver more reliable results in less time, allowing designers and manufacturers to confidently analyze complex structural failures, understand the material composition, and source of defects, and increase yields.

For example, dual beam systems can be used to detect voids in copper interconnect trenches fabricated by a damascene process. In a typical damascene process, the underlying silicon oxide insulating layer of a substrate is patterned with open trenches where the copper conductor should be deposited. A thick coating of copper that significantly overfills the trenches is deposited on the insulator, and chemical-mechanical planarization is used to remove the copper to the level of the top of the insulating layer. Copper that is deposited down in the trenches of the insulating layer is not removed and becomes the patterned conductor. Any voids in the copper within the trenches can cause an open circuit defect. To evaluate the quality of the fill within the trenches, a dual beam system can be used to expose and image a cross section of the trench.

FIG. 1 shows a method for exposing a cross-section using a dual beam SEM/FIB system as known in the prior art. Typically, to analyze a feature within the sample 102, a focused ion beam (FIB) exposes a cross section, or face 108, perpendicular to the top of the surface 112 of the sample material having the hidden feature to be viewed. Because the SEM beam axis 106 is typically at an acute angle relative to the FIB beam axis 104, a portion of the sample in front of the face is preferably removed so that the SEM beam can have access to image the face. One problem with the prior art method is that a large number of cross-sections must typically be exposed along the length of the trench to form a set of samples of a sufficient size to properly characterize the trench.

For features that are deep relative to the opening that is being made by the FIB, the prior art method suffers from a reduced signal to noise ratio. The situation is analogous to shining a flashlight into a deep hole to try to form an image of the side of the hole. For example, a typical copper interconnect trench is 5-8 nanometers (nm) wide by 12 nanometers deep. Many of the electrons from the SEM remain in the trench and are not scattered back to the detector.

A common application for a dual beam system is in the field of biological sciences. For example, electron microscopy allows the observation of molecular mechanisms of diseases, the conformation of flexible protein structures and the behavior of individual viruses and proteins in their natural biological context. One technique employed with electron microscopy for analyzing biological materials, for example, is called "Slice-and-View." This technique is typically performed with a dual beam SEM/FIB system.

In the slice and view technique, the FIB cuts and slices a sample with high precision to reveal its 3D internal structures or features. After obtaining an image of the face by the SEM, another layer of substrate at the face may be removed using the FIB, revealing a new, deeper face and thus a deeper cross-section of the feature. Since only the portion of the feature at the very surface of the face is visible to the SEM, sequential repetition of cutting and imaging, or slicing and viewing, provides the data needed to reconstruct the sliced sample into a 3D representation of the feature. The 3D representation is then used to analyze the sample feature.

The processing of a sample through a slice and view procedure can take a long time if a large section of the sample is processed. This is also true even if the feature of interest is relatively small in relation to the sample because the location of the feature is not typically known with sufficient accuracy to direct the beams of the FIB and SEM to the immediate region of the sample containing the feature. Therefore, a large section of the sample suspected of having the feature is processed in order to locate the feature. With a typical maximum field of view for the SEM being about 150 microns, slice milling and imaging an area this size can be a significant time investment, especially with high resolution settings on the SEM. Alternatively, many smaller portions of the area may be imaged, but doing so generates a vast amount of image data, and the resulting images are typically required to be stitched together to form a larger composite image. Such processes currently can last anywhere from a few hours to several days.

In prior art methods a relatively large section has been required to be processed with every iteration of the slice and view procedure because the shape or direction of the feature through the sample has not been accurately predicted. This problem is especially exacerbated with certain features that have long, winding shapes through the sample, such as is the case with blood vessels or nerves.

SUMMARY OF THE INVENTION

An embodiment of the present invention is directed to a method of forming a planar cross-section view for an electron microscope. The method comprises directing an ion beam from an ion source toward a first surface of a sample to mill at least a portion of the sample. The method further comprises milling the first surface, using the ion beam, to expose a second surface in which the end of the second surface distal to the ion source is milled to a greater depth relative to a reference depth than the end of the first surface proximal to the ion source. The method further comprises directing an electron beam from an electron source to the second surface. The method further comprises forming an image of the second surface by detecting the interaction of the electron beam with the second surface.

Another embodiment of the present invention is directed to a method for forming a cross-section view for an electron microscope. The method comprises directing an ion beam from an ion source toward a first surface of a sample to mill at least a portion of the sample; milling the first surface at least in the local area of a feature of interest using the ion beam to make the first surface at least in the local area of the feature of interest substantially planar; subsequent to milling the first surface, milling the sample to expose a second surface, the second surface comprising a cross-section of the feature of interest; directing an electron beam from an electron source to the second surface; and forming an image of the second surface by detecting the interaction of the electron beam with the second surface.

Another embodiment of the present invention is directed to a system for forming a planar cross section view for an electron microscope, the system comprising a focused ion beam column; an electron microscope; a sample stage for holding a sample; and a computer controller. The computer controller includes a non-transitory computer-readable medium encoded with computer instructions that when executed by the computer controller, cause the system to: direct an ion beam from an ion source toward a first surface of a sample to mill at least a portion of the sample; mill the first surface, using the ion beam, to expose a second surface in which the end of the second surface distal to the ion source is milled to a greater depth relative to a reference depth than the end of the first surface proximal to the ion source; direct an electron beam from an electron source to the second surface; and form an image of the second surface by detecting the interaction of the electron beam with the second surface.

Another embodiment of the present invention is directed to a system for forming a cross section view for an electron microscope, the system comprising a focused ion beam column; an electron microscope; a sample stage for holding a sample; and a computer controller. The computer controller includes a non-transitory computer-readable medium encoded with computer instructions that when executed by the computer controller, cause the system to: direct an ion beam from an ion source toward a first surface of a sample to mill at least a portion of the sample; mill the first surface at least in the local area of a feature of interest using the ion beam to make the first surface at least in the local area of the feature of interest substantially planar; subsequent to milling the first surface, mill the sample to expose a second surface, the second surface comprising a cross-section of the feature of interest; direct an electron beam from an electron source to the second surface; and form an image of the second surface by detecting the interaction of the electron beam with the second surface.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

Preferred embodiments of the present invention are directed at a novel method of defect analysis suitable for use in semiconductor fabrication, although the present invention can be used in the analysis of other sample types as described below. In order to analyze a semiconductor chip, for example a chip containing metal milled trenches, rather than using an orthogonally oriented FIB to expose a sequence of cross-sections as in the prior art, sample analysis according to a preferred embodiment of the present invention makes use of a glancing angle mill in which the FIB is oriented at a very small angle to the sample surface, preferably at an angle no greater than 10°.

Figure 1:
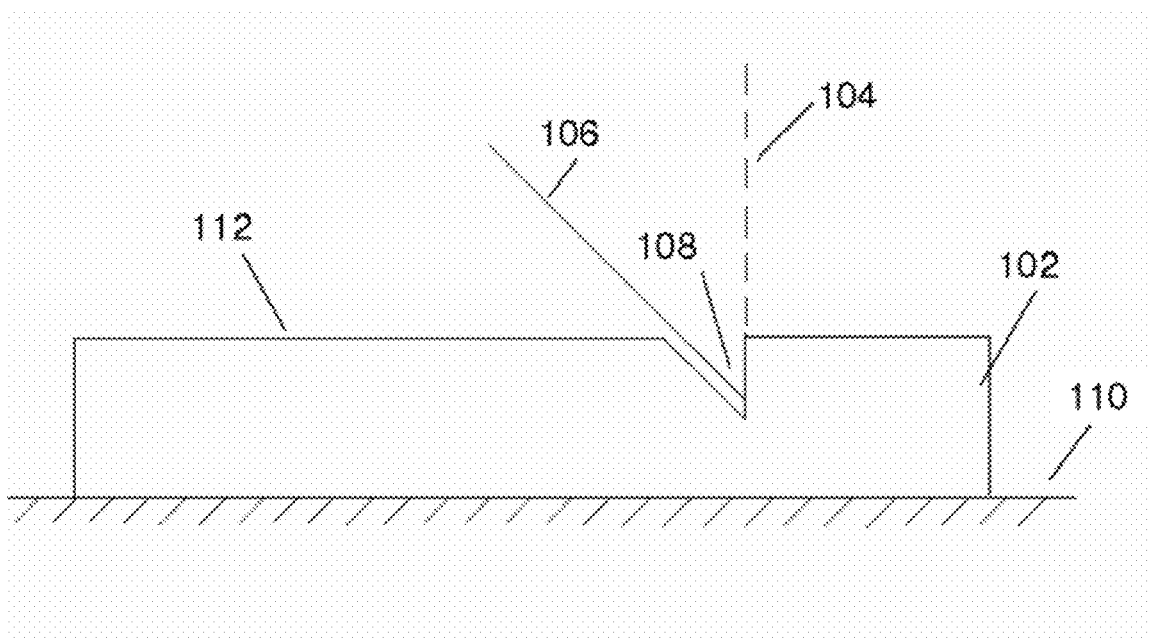
FIG. 1 shows a method for exposing a cross-section using a dual beam SEM/FIB system as known in the prior art.
Figure 2:
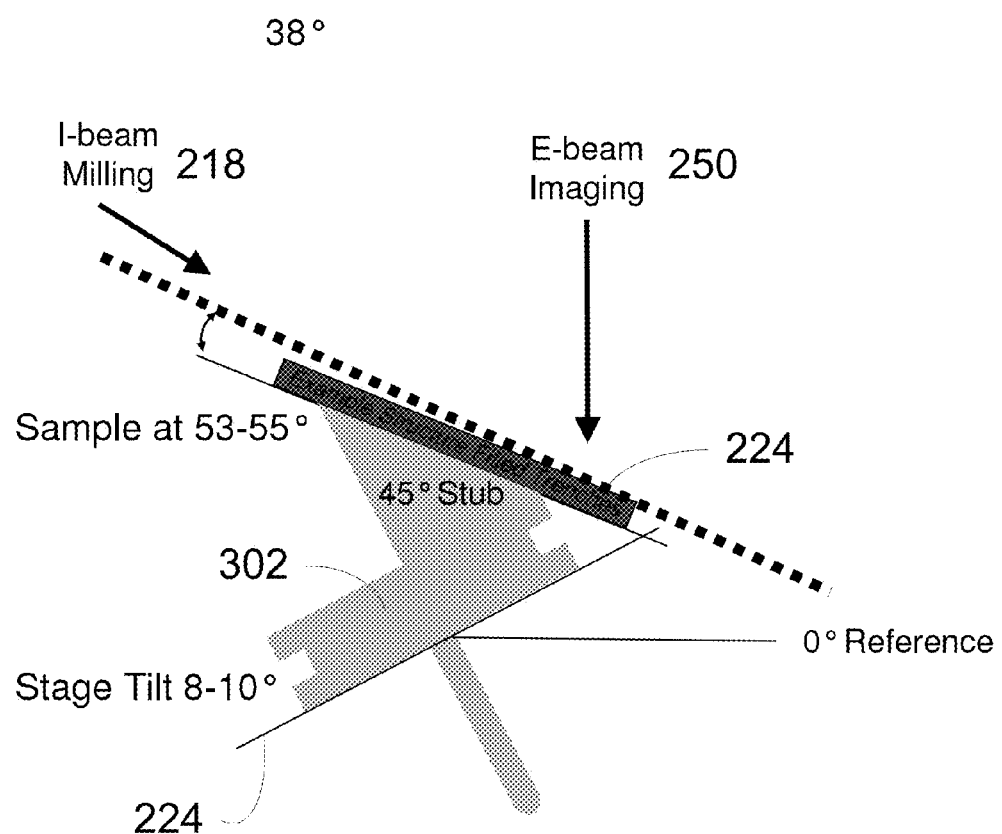
FIG. 2 shows a sample orientation in a dual beam system for forming planar cross section view for a scanning electron microscope in accordance with one or more embodiments of the present invention.

Because the ion beam is oriented at such a small angle relative to the sample surface, as shown in FIG. 2 discussed below, the amount of sample material milled away will be greater opposite the ion source. That is, the exposed surface is milled to a greater depth on the end of the sample that is farthest from the ion source than the end that is closest to the ion source. This causes the exposed surface to have a downward slope relative to the original sample surface. For sample features such as rows of metal-filled trenches, the trenches closest to the ion source will have an upper portion of the trenches exposed, while deeper portion of the trenches further away from the ion source will be exposed. Once the sloped sample surface has been exposed, the exposed face can then be imaged from the top down, for example with an electron beam. The image of the exposed sloped face will essentially be a combination of a planar view and multiple cross section views in terms of the structural information provided.

FIG. 2 shows an ion beam milling the top surface of sample 222 at a glancing angle in accordance with one or more embodiments of the present invention. In the embodiment of FIG. 2, sample 222 is mounted on a standard 45° pre-tilted sample stub 302, which is in turn mounted on a tilting sample stage 224 in an ion beam system such as a dual beam SEM/FIB. Suitable dual beam systems are commercially available, for example, from FEI Company, Hillsboro, Oreg., the assignee of the present application. While an example of suitable hardware is provided below, the invention is not limited to being implemented in any particular type of hardware. In the embodiment of FIG. 2, the electron beam and the ion beam are oriented with the electron beam 250 normal to an untilted sample stage and the ion beam 218 at an angle of approximately 52°. In other embodiments, pre-tiled sample stub 302 is not used and the tilt of the sample is set by sample stage tilt and/or column tilt.

As shown in FIG. 2, the stage is tilted so that the ion beam is located a slight glancing angle with respect to the sample surface. Preferably the glancing angle is 10° or less, more preferably 5° or less, or even more preferably 1° or less. As used herein, a glancing angle mill will refer to milling a sample with the angle between the ion beam and the top surface of the being 10° or less. In the embodiment shown in FIG. 2, a suitable glancing angle results from the use of the 45° sample stub and a stage tilt of 8°-10°. Ion beam 218 is thus directed at the top surface of sample 222 at a glancing angle of only 1-3 degrees.

The actual angle used will depend on the system being used and the depth of the measurement to be made. For example, a typical copper interconnect trench is 12 nanometers (nm) deep. The tilt of sample stage 224 is adjusted so that the angle between ion beam 218 and sample 222 will make a cut that is 12 nm deep at the distal end of target area 300. Skilled persons will recognize that, although in the embodiment of FIG. 2, the ion beam is directed at the very upper surface of the sample, in some preferred embodiments the beam could be directed deeper into the sample to expose more deeply buried features in much the same fashion.

Figure 3:
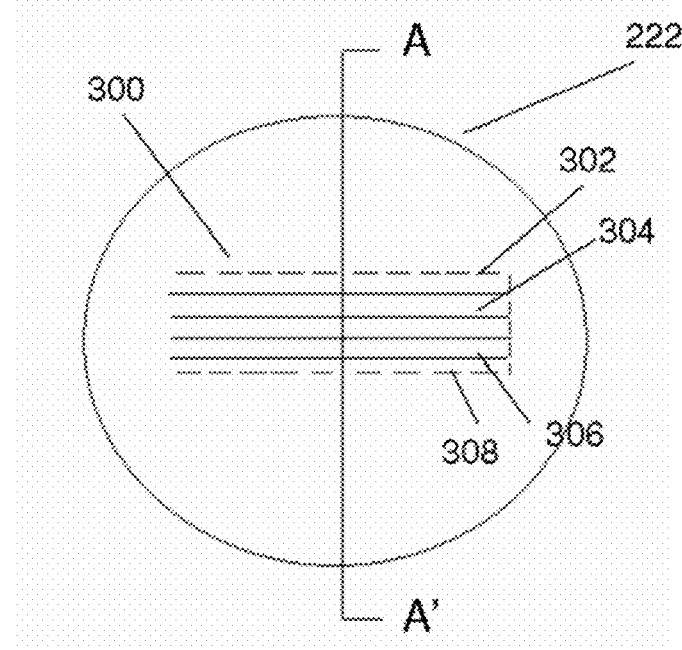
FIG. 3 shows a target area 300 of sample 222 comprising a plurality of features 302-308 for which is it desired to form an SEM image of the features at various lengths along the features within target area 300.

FIG. 3 shows a target area 300 of sample 222 comprising a plurality of features 302-308 for which is it desired to form an SEM image of the features at various lengths along the features within target area 300. For example, sample 222 can be a wafer containing copper interconnects trenches formed in a damascening process. Target area 300 is a portion of sample 222 containing trenches 302-308 for which it is desired to detect any copper voids that may have formed in trenches 302-308 during the damascening process. Although much of the description herein is directed at preferred embodiments where the sample to be analyzed is a semiconductor chip, embodiments of the present invention could also be directed at other types of samples, such as biological or geological samples, where a similar analysis is desired.

Figure 4:
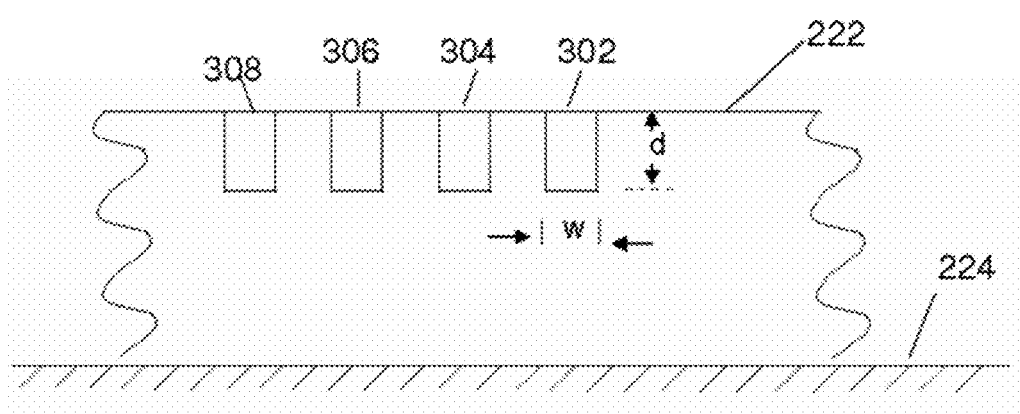
FIG. 4 shows a cross-section of sample 222 taken along cut line A-A' shown in FIG. 3.
Figure 5:
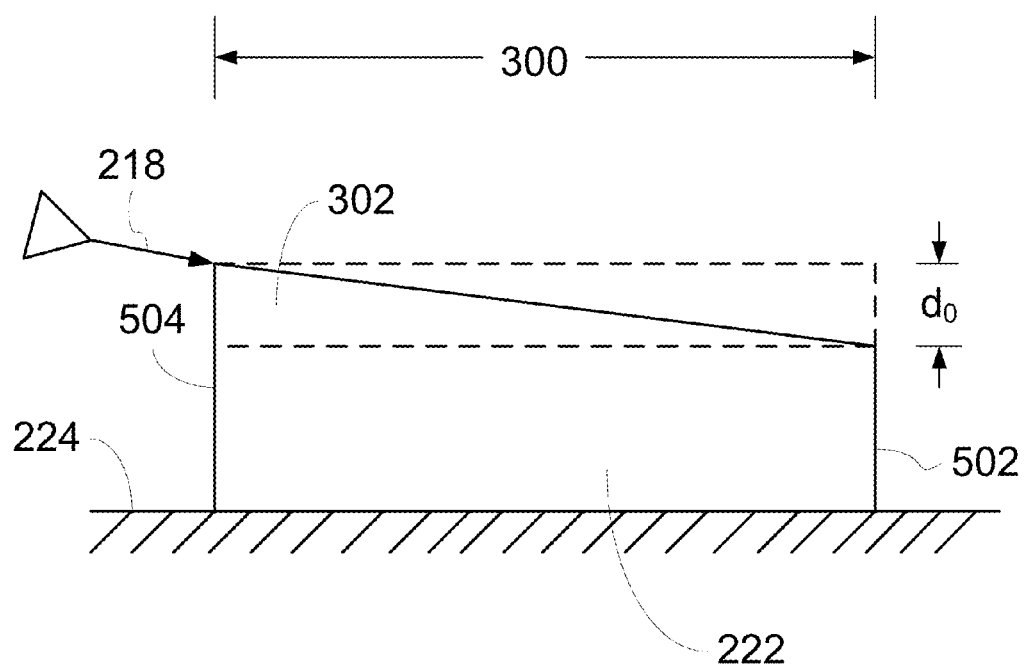
FIG. 5 shows an ion beam milling the top surface of sample 222 at a glancing angle in accordance with one or more embodiments of the present invention.

FIG. 4 shows a cross-section of sample 222 taken along cut line A-A' shown in FIG. 3. Features 302-308 extend from the top surface of sample 222 a given depth (d) into sample 222. For example, a typical copper interconnect trench is 5-8 nanometers (nm) in width (w) and 12 nm in depth (d). To check for defects using prior art methods, a series of time-consuming cross-section cuts would have to be made along the length of target area 300. Then each of the cross sections is individually imaged by the SEM. As shown in FIG. 5, one or more embodiments of the present invention enables the detection of feature defects with improved cycle time and signal to noise ratio.

FIG. 5 shows an ion beam milling the top surface of sample 222 at a glancing angle in accordance with one or more embodiments of the present invention. According to preferred embodiments of the present invention, the glancing angle is an edge-directed milling angle instead of a top-down milling angle. That is, instead of being directed at a nearly perpendicular angle to the top surface of sample 222 to expose a vertical face with a series of vertical cuts, ion beam 218 is directed at sample 222 from an edge of the sample at a very acute "glancing" angle between the ion beam and the top surface prior milling. The angle is chosen so that, over the length of target area 300, ion beam 218 mills the top surface sample 222 to a predetermined depth ($d_0$) at the end of target area 300 that is distal to ion source 214. After milling, a surface of the sample is exposed with in target area 300 in which the distal end 502 of the target area is milled to a greater the depth relative to the bottom surface of sample 222 than the depth, if any, to which the proximal end 504 of the top surface of sample 222 within the target area is milled.

The effect of milling at a glancing angle is that, with a single cut from ion beam 218, features 302-308 (only feature 302 is shown) is exposed at varying depths along the length of feature 302, at least within target area 300. The SEM then images the features 302-308 at various locations along the length of target area 300 to characterize the feature at those locations. Each location corresponds to a different depth based on the angle at which sample 222 was milled and the distance of the location from the proximal edge of the cut. This is shown in FIGS. 6 and 7.

Figure 6:
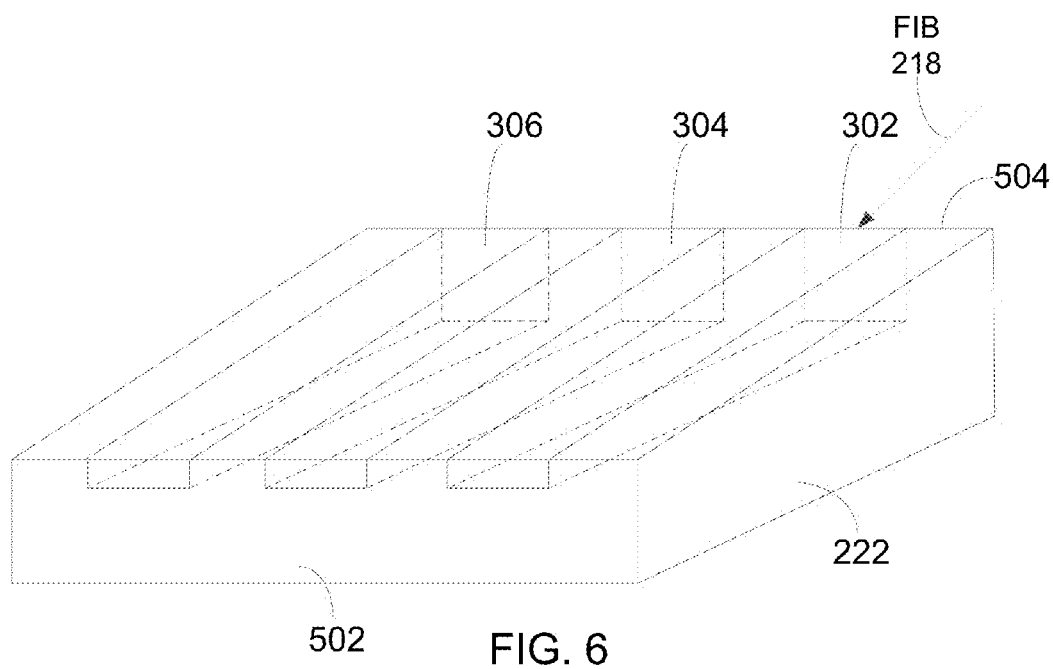
FIG. 6 shows an oblique view of a sample target area after glancing angle milling in accordance with one or more embodiments of the present invention.
Figure 7:
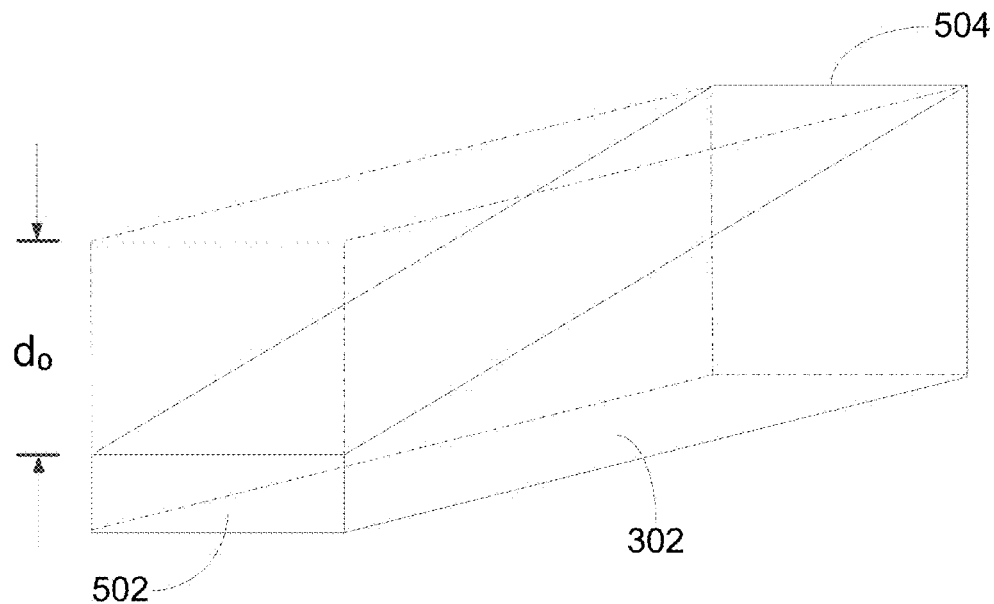
FIG. 7 shows an oblique view of feature 302 after milling.

FIG. 6 shows an oblique view of a sample target area after glancing angle milling in accordance with one or more embodiments of the present invention. The distal end 502 of sample 222 is milled to a greater depth than the proximal end 504, and the surface of the sample slopes linearly between the two ends. FIG. 7 shows an oblique view of feature 302 after milling Feature 302 is milled to predetermined depth d0 at the distal end 502 of the feature. Feature 302 is milled very little, if at all, at the proximal end 504 of the feature. The SEM is used to image along the length of feature 302. Because the glancing angle mill causes the surface of feature 302 to gradually slope from a depth of 0 nm to d0 nm, the SEM can characterize the feature at various depths by forming an image at corresponding locations along the length of feature 302. Milling individual cross-sectioning cuts at each of those locations is not necessary, thereby resulting in an improved cycle time for defect analysis.

Further, embodiments of the present invention can also provide improved imaging of the sample face as compared to typical cross-section cuts. Using the prior art method of sequentially exposing cross section faces in a sample, typically a wedge shaped hole is milled into the sample to expose the sample face and to provide sufficient room for the exposed face to be imaged, for example by an electron beam. When the cross-section face is imaged, some of the secondary electrons which would otherwise be used to help for the image are lost because they impact upon the sides of the wedge shaped hole. As a result, signal strength is lost and the signal to noise ratio is degraded. According to one or more embodiments of the present invention, however, no hole is milled into the sample to expose a cross-section. Instead, the glancing angle mill produces a sloping surface which is more easily imaged and which results in improved signal to noise as compared to the prior art.

Figure 8:
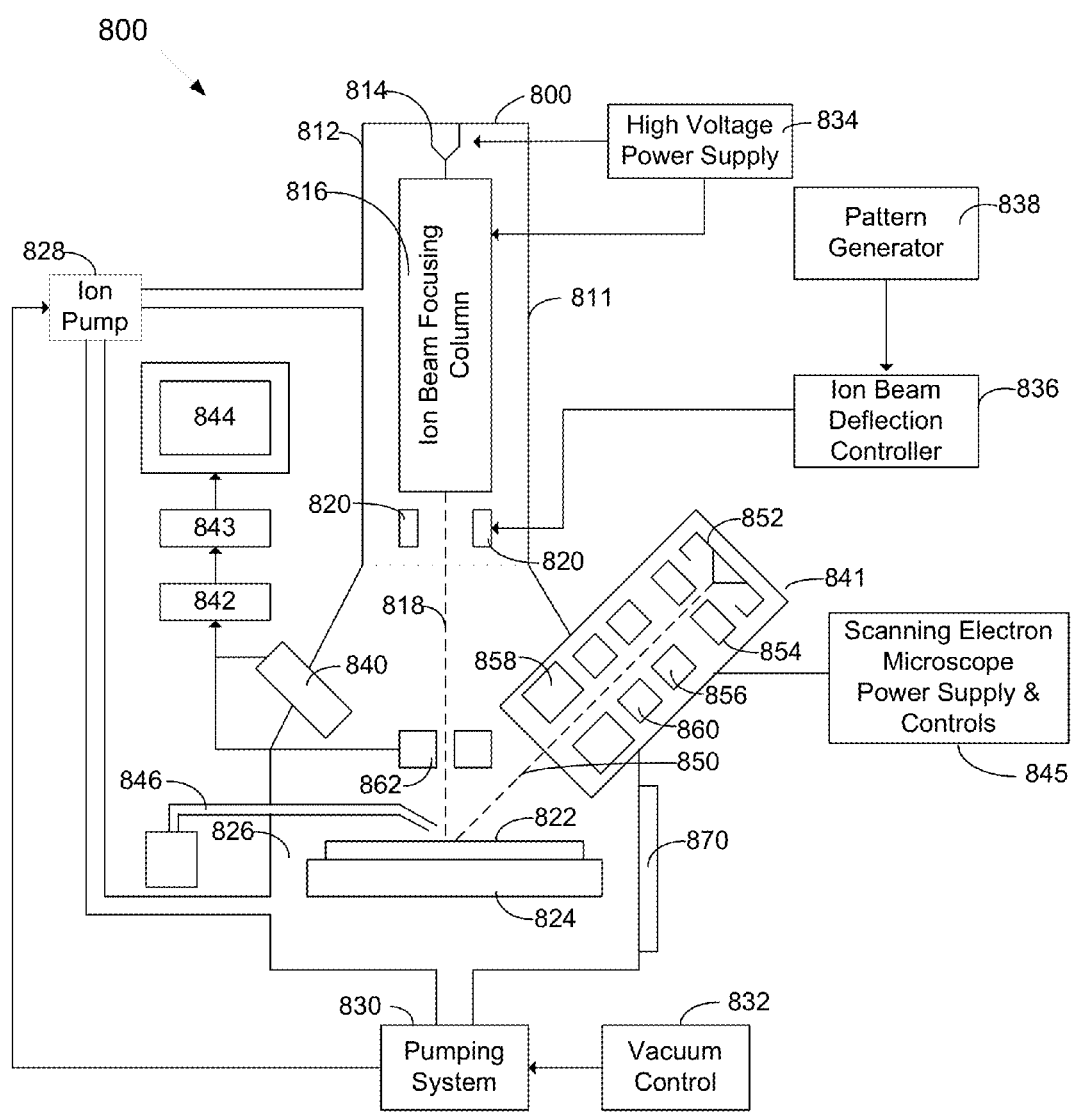
FIG. 8 shows an exemplary dual beam FIB/SEM system that could be used to implement one or more embodiments of the present invention.

FIG. 8 shows a typical dual beam FIB/SEM system 800 used to implement one or more embodiments of the present invention. Focused ion beam system 800 includes an evacuated envelope 811 having an upper neck portion 812 within which are located an ion source 814 and a focusing column 816 including extractor electrodes and an electrostatic optical system. Ion beam 818 passes from ion source 814 through column 816 and between electrostatic deflection means schematically indicated at 820 toward sample 822, which comprises, for example, a semiconductor device positioned on movable sample stage 824 within lower chamber 826. An ion pump 828 is employed for evacuating neck portion 812. The chamber 826 is evacuated with turbomolecular and mechanical pumping system 830 under the control of vacuum controller 832. The vacuum system provides within chamber 826 a vacuum of between approximately 1×10-7 Torr and 5×10-4 Torr. If an etch assisting gas, an etch retarding gas, or a deposition precursor gas is used, the chamber background pressure may rise, typically to about 1×10-5 Torr.

High voltage power supply 834 is connected to ion source 814 as well as to appropriate electrodes in focusing column 816 for forming an ion beam 818 and directing the same downwardly. Deflection controller and amplifier 836, operated in accordance with a prescribed pattern provided by pattern generator 838, is coupled to deflection plates 820 whereby beam 818 may be controlled to trace out a corresponding pattern on the upper surface of sample 822. In some systems the deflection plates are placed before the final lens, as is well known in the art.

The ion source 814 typically provides a metal ion beam of gallium, although other ion sources, such as a multicusp or other plasma ion source, can be used. The ion source 814 typically is capable of being focused into a sub one-tenth micron wide beam at sample 822 for either modifying the sample 822 by ion milling, enhanced etch, material deposition, or for the purpose of imaging the sample 822. A charged particle multiplier 840 used for detecting secondary ion or electron emission for imaging is connected to amplifier 842. The amplified signals are converted into digital signals and subjected to signal processing by the signal processor unit 843. The resulting digital signal is to display an image of workpiece 822 on the monitor 844.

A scanning electron microscope 841, along with power supply and control unit 845, is also provided with the FIB system 800. An electron beam 850 is emitted from a cathode 852 by applying voltage between cathode 852 and an anode 854. Electron beam 850 is focused to a fine spot by means of a condensing lens 856 and an objective lens 858. Electron beam 850 is scanned two-dimensionally on the specimen by means of a deflection coil 860. Operation of condensing lens 856, objective lens 858, and deflection coil 860 is controlled by power supply and control unit 845.

Electron beam 850 can be focused onto workpiece 822, which is on sample stage 824 within lower chamber 826. When the electrons in the electron beam strike workpiece 822, secondary electrons are emitted. These secondary electrons are detected by secondary electron detector 840 or by backscattered electron detector 862, which are connected to an amplifier 842. The amplified signals are converted into digital signals and subjected to signal processing by the signal processor unit 843. The resulting digital signal is to display an image of workpiece 822 on the monitor 844.

A gas delivery system 846 extends into lower chamber 826 for introducing and directing a gaseous vapor toward sample 822. U.S. Pat. No. 5,851,413 to Casella et al. for "Gas Delivery Systems for Particle Beam Processing," assigned to the assignee of the present invention, describes a suitable fluid delivery system 846. Another gas delivery system is described in U.S. Pat. No. 5,435,850 to Rasmussen for a "Gas Injection System," also assigned to the assignee of the present invention.

A door 870 is opened for inserting sample 822 onto sample stage 824, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam column 816 for energizing and focusing ion beam 818. Dual beam FIB/SEM systems are commercially available, for example, from FEI Company, Hillsboro, Oreg., the assignee of the present application.

Figure 9:
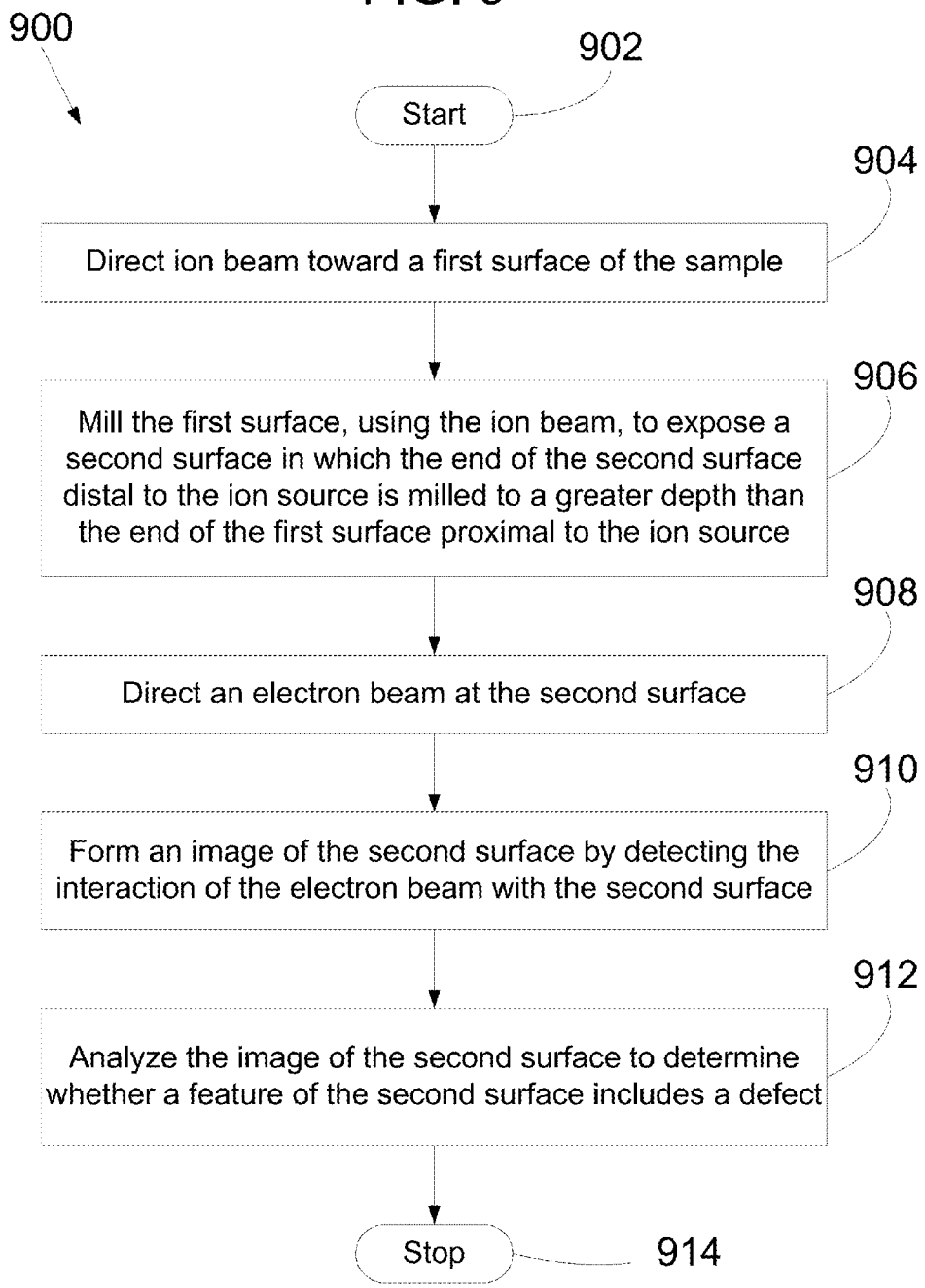
FIG. 9 is a flowchart showing the steps of performing a sample analysis according one or more embodiments of the present invention.

FIG. 9 is a flowchart 900 showing the steps of performing a sample analysis according one or more embodiments of the present invention. The process begins at terminator 902. At step 904, ion beam 818 is directed at a first surface of sample 822 to mill at least a portion of sample 822. In a preferred embodiment, the first surface is the top surface of sample 822 and ion beam is 818 is directed at a glancing angle near an edge of the top surface instead of being directed at a nearly perpendicular angle to the top surface. At step 906, ion beam 818 mills the first surface to expose a second surface in sample 822 in which the end of the second surface distal to ion source 814 is milled to a greater depth relative to a reference depth than the end of the first surface proximal to ion source 814. That is, along the length of the exposed second surface, the end of the second surface farther from the beam source is milled to a greater depth than the end of the second surface closest to the beam source. The difference in depth is due to the angle of the beam with respect to the first surface. Because the angle is a glancing angle, the difference in depth along the entire second surface can be made to be only as deep at the feature that is to be analyzed based. At step 908, electron beam 850 from SEM 841 is directed to the second surface for form an image of the second surface. At step 910, an image of at least a portion of the second surface is formed by detecting the interaction of the electron beam with the second surface. For example, secondary electron detector 840 or backscattered electron detector 862 can be used to form an image from the secondary electrons that are emitted when electron beam 850 is directed at the second surface of sample 822. At step 912, the imaged formed in step 910 is analyzed to determine whether a feature of the second surface has a defect. For example, if the sample is a semiconductor wafer having copper interconnect trenches, the image formed according to the method of FIG. 9 can be analyzed to determine the quality of the fill of the trenches, that is, to detect voids in the trenches during plating. In a slice and view application, the image can be used as one of a plurality of slices used to make up a three-dimensional structure of the feature.

Glancing angle milling can be used to planarize a localized area of the sample surface. The entire length of the top surface of sample 822 need not be milled. In some embodiments of the present invention, only a portion of the length of the top surface of sample 822 is milled. A glancing angle mill can be performed to planarize a local area near a feature of interest of a sample having an irregular surface to reduce or prevent curtaining during a subsequent cross-section mill operation. Curtaining occurs when material is removed at different milling rates. This can happen when milling a feature comprised of materials that are removed at different rates by the same beam. This can also happen when milling a surface that has an irregular shape. For example, the feature of interest can be a through-silicon vias (TSVs). Cross-sectioning TSVs is a common practice in semiconductor labs to characterize voids and surface interfaces. Due to the depth of TSVs (typically 50-300 nm), milling a cross section of a TSV with an ion beam can result in substantial curtaining. Planarizing the sample surface in the local area of the TSV with a glancing angle mill before performing a cross-section mill of the TSV can reduce or prevent curtaining during the cross-section mill.

Figure 10:
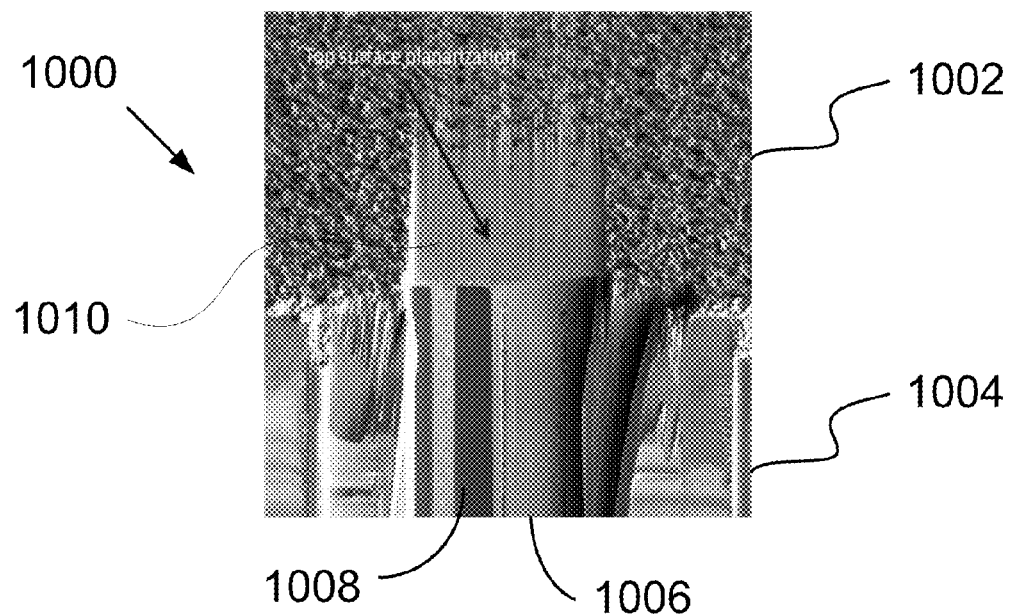
FIG. 10 is an SEM micrograph showing top surface planarization of a sample and a cross section of a through-silicon via.

FIG. 10 is an SEM micrograph showing top surface planarization of a sample and a cross section of a through-silicon via. Micrograph 1000 shows a sample having a top surface 1002, a side surface 1004, a top surface planarizing cut 1010, a cross-section cut 1006, and a through-silicon via 1008. Top surface 1002 of the sample has an irregular shape, which makes top-down cross-sectioning cuts prone to curtaining. For example, top surface 1002 may be a protective layer deposited on the sample prior to cross-sectioning, such as a protective layer of platinum. A glancing angle mill is placed on the portion of top surface 1002 that is located above TSV 1008. The glancing angle mill planarizes top surface 1002 in the local area above TSV 1008, reducing or removing the surface irregularity. After the glancing angle mill is performed to planarize top surface 1002 in the local area above TSV 1008, a cross-sectioning mill is performed to expose a cross-section of TSV 1008. Because top surface 1002 is planarized in the local area above TSV 1008, curtaining in cross-section cut 1006 is reduced or eliminated, providing a better cross-section of TSV 1008 for subsequent analysis.

Figure 11:
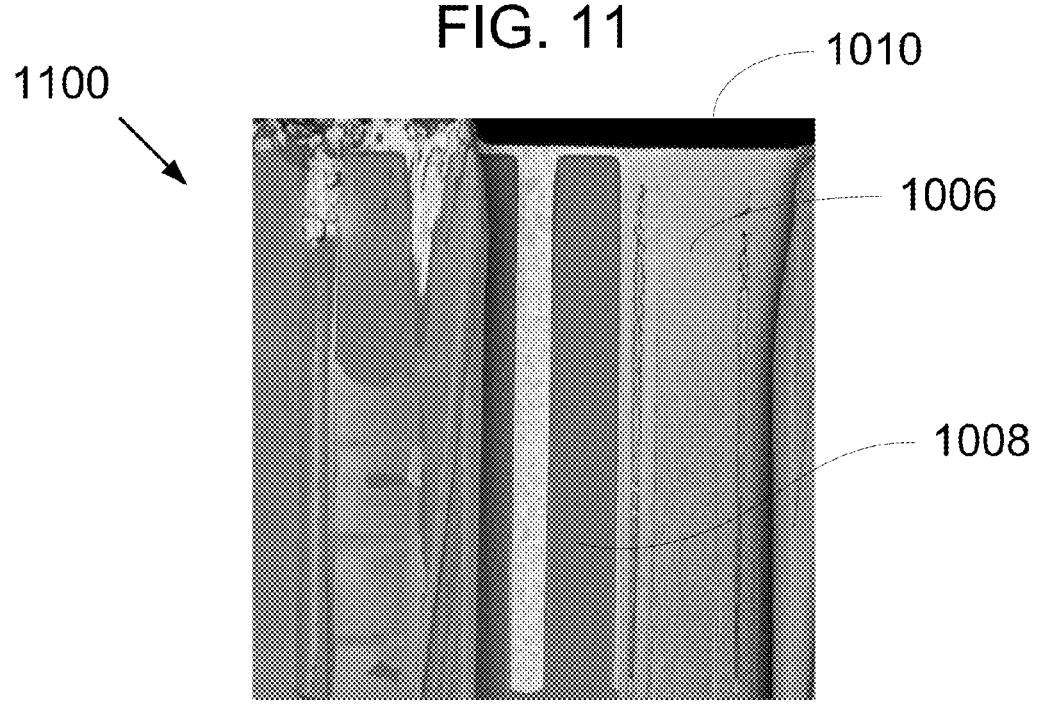
FIG. 11 is an SEM micrograph showing a cross-section view of the sample of FIG. 10, the cross section being milled after top surface planarization by a glancing angle mill.

FIG. 11 is an SEM micrograph showing a cross-section view of the sample of FIG. 10, the cross section being milled after top surface planarization by a glancing angle mill. Top surface planarizing cut 1010 makes the local area of the sample surface above TSV 1008 substantially planar. As a result, curtaining in the subsequently milled cross-section cut 1006 is substantially reduced or eliminated, providing a better cross-section of TSV 1008 for subsequent analysis.

Although the description of the present invention above is mainly directed at methods of sample analysis, it should be recognized that an apparatus performing the operation of such a method would further be within the scope of the present invention. Further, it should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "analyzing", "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor chip" refers generically to an integrated circuit (IC), which may be integral to a semiconductor wafer, singulated from a wafer, or packaged for use on a circuit board. The term "FIB" or "focused ion beam" is used herein to refer to any collimated ion beam, including a beam focused by ion optics and shaped ion beams.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of forming a planar cross-section view for an electron microscope, the method comprising:
   directing an ion beam at a milling angle from an ion source toward a first surface of a sample to mill at least a portion of the sample, in which the milling angle between the ion beam and the first surface is equal to or less than ten degrees;
   milling the first surface, using the ion beam directed at the milling angle, to expose a second surface in which the end of the second surface distal to the ion source is milled to a greater depth relative to a reference depth than the end of the first surface proximal to the ion source, the second surface including at least one feature of interest;
   directing an electron beam from an electron source to the second surface; and
   forming an image of the second surface by detecting the interaction of the electron beam with the second surface, the image including at least a portion of the feature of interest;
   characterizing the feature of interest in a plurality of locations along the image of the second surface; and
   determining a depth of each of the plurality of locations based on the distance of the location from the end of the image proximal to the ion source and the milling angle between the ion beam and the first surface.

2. The method of claim 1 further comprising analyzing the image of the second surface to determine whether a feature of the second surface includes a defect.

3. The method of claim 1 in which the milling angle between the ion beam and the first surface is equal to or less than five degrees.

4. The method of claim 1 in which the milling angle between the ion beam and the first surface is equal to or less than one degree.

5. The method of claim 1 in which the ion beam comprises a focused ion beam.

6. The method of claim 1 in which the tilt of a sample stage, upon which the sample is mounted, is changed between the milling step and the image forming step.

7. The method of claim 1 in which a 45 degree stub is disposed between the sample stage and the sample.

8. The method of claim 1 in which milling the first surface using the ion beam to expose the second surface further comprises:
   milling the first surface at least in the local area of a feature of interest using the ion beam to make the first surface at least in the local area of the feature of interest substantially planar;
   subsequent to milling the first surface, milling the sample using the ion beam directed at the milling angle to expose a second surface, the second surface comprising a cross-section of the feature of interest.

* * * * *